United States Patent [19]

Carmichael

[11] 4,213,965

[45] Jul. 22, 1980

[54] SMALL-PLAQUE VARIANT CANINE HERPESVIRUS VACCINE

[75] Inventor: Leland E. Carmichael, Ithaca, N.Y.

[73] Assignee: Cornell Research Foundation, Inc., Ithaca, N.Y.

[21] Appl. No.: 5,743

[22] Filed: Jan. 23, 1979

Related U.S. Application Data

[63] Continuation-in-part of Ser. No. 959,808, Nov. 13, 1978, abandoned.

[51] Int. Cl.² ............................................. A61K 39/12
[52] U.S. Cl. ...................................... 424/89; 435/237
[58] Field of Search ...................... 424/89; 195/1.1–1.3

[56] References Cited

PUBLICATIONS

Carmichael et al., Infection and Immunity 20(1):108–114, Apr. 1978, Small-Plaque Variant of Canine Herpesvirus with Reduced Pathogenicity for Newborn Pups.

*Primary Examiner*—Shep K. Rose
*Attorney, Agent, or Firm*—Jones, Tullar & Cooper

[57] ABSTRACT

This invention relates to a vaccine against Canine Herpesvirus from a newly isolated small-plaque variant of Canine Herpesvirus, and to a method for producing small-plaque variant reduced pathogenicity canine herpesvirus.

14 Claims, 4 Drawing Figures

GROWTH OF MP (●) AND mP (○) STRAINS OF CHV AT 30°C (BROKEN LINES) AND AT 35°C (SOLID LINES).

FIG. 3

INACTIVATION KINETICS OF MP (●) AND mP (△)
STRAINS OF CHV AT 38° C

FIG. 4

GROWTH OF MP (●) AND mP (○) STRAINS OF CHV AT
30° C (SOLID LINES) AND AT 37°C (BROKEN LINES)
IN CANINE SPLEEN CELLS. TITERS REPRESENT CELL-
ASSOCIATED VIRUS.

SMALL-PLAQUE VARIANT CANINE HERPESVIRUS VACCINE

CROSS REFERENCE TO RELATED APPLICATION

This application is a continuation-in-part of application Ser. No. 959,808, filed Nov. 13, 1978, now abandoned.

BACKGROUND OF THE INVENTION

Canine herpesvirus (CHV) is an important cause of the deaths of neonatal pups; however, the disease caused by this virus is inapparent in older animals; Carmichael, *J. Am. Vet. Med. Assoc.* 156: 1714-1721 (1970); Carmichael et al, *Am. J. Vet. Res.*, 26: 802-814 (1965). The dog is the only known host, and viral growth occurs exclusively in cells of canine origin; Carmichael et al, *Proc. Soc. Exp. Biol. Med.*, 120: 644-650 (1966). Growth of CHV is markedly restricted by the temperature of incubation, the optimal range being 35° to 37° C.; Aurelian, *Am. J. Vet. Res.*, 30: 1945-1952 (1968); Carmichael et al, *J. Am. Vet. Med. Assoc.*, 120: 664-668 (1970). Plaque characteristics of several field isolates grown at optimal temperatures in primary dog kidney cell (DKC) cultures have appeared consistent in size and character (Pryde et al, *Vet. Rec.*, 79: 660-661 (1966); Spertzel et al, *Proc. Soc. Exp. Biol. Med.*, 120: 651-655 (1965)), with the unique exception of the BR strain isolated in England from the genital tract of dogs in vesicular lesions; Poste, *Arch. Gesamte Virusforsch.*, 36: 147-157 (1972). The BR strain of CHV was unusual in that it caused plaques on DKC monolayers consisting principally of polykaryocytes. Unfortunately, it was apparently not preserved in a viable state.

The recognition of natural plaque mutants of several animal viruses has facilitated the exploration of viral genetics; in some instances plaque characteristics also have been associated with differences in strain virulence and have been exploited for vaccine; Darlington et al, *The Herpesviruses* (Kaplan, ed.) Academic Press Inc., New York, 1973, pages 93-132; Takemoto, *Prog. Med. Virol.*, 8: 314-348 (1966). Herpesvirus plaque morphology has been used as a biological marker for genetic studies (Arlington et al and Takemoto, supra), as well as for discriminating closely related strains; Cho, *Avian Dis.*, 20: 324-331 (1976); Lancz, *Arch. Gesamte Virusforsch.*; 46: 31-43 (1974); Monk et al, *Arch. Gesamte Virusforsch.*; 37: 308-315 (1972). Plaque characteristics of Marek's disease herpesvirus (MDHV) in natural host cells also have proved useful in the preliminary assessment of strain virulence; Biggs et al *Oncogenesis and Herpeviruses* (Biggs et al ed.), WHO International Agency for Research on Cancer, Lyon (1972) Pages 88-94; Cho, *Avian Dis.*, 20: 324-331 (1976).

Herpesvirus virulence has been associated with a variety of other in vitro properties, including the type of cytopathology, viral growth characteristics at difference temperatures, antigenic differences, host cell range, resistance to 5-iododeoxyuridine, and plaque characteristics in alien host cells; Cho, supra; Darlington, supra; Koment et al, *Intervirology*, 5: 10-20 (1975); Pryde, supra; Tokumaru, *Proc. Soc. Exp. Biol. Med.*, 96: 55-58 (1957). *Herpesvirus homines* (HVH) types have been studied extensively. With this virus, differences in plaque morphology have permitted the clear discrimination between strains; Monk et al, supra; Roizman, *Virology*; 15: 75-79 (1961). An HVH-1 strain that produced small plaques in rabbit kidney cells also was found to be less virulent for rabbits and mice than the wild-type (large plaque) virus; Rapp et al, *Proc. Soc. Exp. Biol. Med.*, 166: 361-365 (1964).

BRIEF DESCRIPTION OF THE INVENTION

It has now been proven that canine herpesvirus passaged in a canine herpesvirus growth supporting tissue culture at suboptimal temperatures produces a small plaque variant (an mP strain), which lacks pathogenicity for newborn pups, but which when employed as a vaccine for canines imparts resistance against virulent canine herpesvirus strains.

BRIEF DESCRIPTION OF THE DRAWINGS

FIG. 2 is a graphic representation of the growth of MP and mP strains of CHV at 30° C. and 35° C.

FIG. 3 is a graphic representative of the inactivation kinetics of MP and mP strains of CHV at 38° C.

FIG. 4 is a graphic representation of the growth of MP and mP strains of CHV at 30° C. and 37° C. in canine spleen cells.

DETAILED DESCRIPTION OF THE INVENTION

Figure 1:
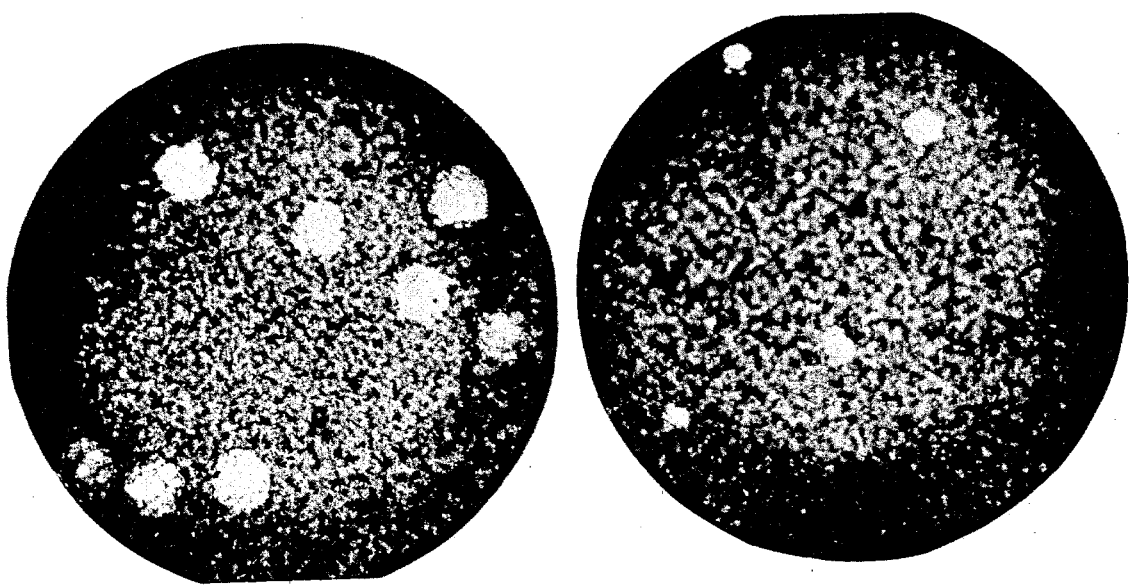
FIG. 1 shows the relative plaque morphology of CHV strains the left hand photo being the MP (wild-type) with the right hand photo being the mP (variant) at the same scale.

It has now been discovered that canine herpesvirus passaged in a canine herpesvirus growth supporting tissue culture at suboptimal temperatures process a small plaque variant which lacks pathogenicity yet imparts resistance to virulent CHV, when employed as a vaccine in bitches or new born pups.

Analysis of the plaque characteristics of 14 CHV strains isolated at various times and from different geographical areas reveals an overall mean plaque size of 1.50±0.09 mm at 35° C. Plaques produced by the different field strains did not differ significantly in size (P<0.01).

TABLE 1.

History and mean plaque size of different CHV strains in DKC monolayer cultures after 5 days of growth at 30° and 35° under a 1% methylcellulose overlay medium

| Strain | Geographical source(yr) | Tissue source[a] | DKC cultures | Plaque size (mm) 30° C. | Plaque size (mm) 35° C. |
|---|---|---|---|---|---|
| F-205 | New York ('61) | Lung | 2 | 0.6 ± 0.05 | 1.50 ± 0.12 |
| F-205-MP | New York ('61) | Lung | 312 | 0.6 ± 0.09 | 1.50 ± 0.15 |
| F-205-mP | New York ('61) | Lung | —[b] | 0.65 ± 0.03 | 0.75 ± 0.04 |
| G 4/66 | Georgia ('66) | Spleen | 3 | 0.57 ± 0.07 | 1.56 ± 0.05 |
| M 4/66 | Maryland ('66) | Kidney | 2 | 0.62 ± 0.05 | 1.48 ± 0.04 |
| O 3/66 | Ontario ('66) | Urine | ? | 0.58 ± 0.07 | 1.50 ± 0.08 |

TABLE 1.-continued

History and mean plaque size of different CHV strains in DKC monolayer cultures after 5 days of growth at 30° and 35° under a 1% methylcellulose overlay medium

| Strain | Geographical source(yr) | Tissue source[a] | DKC cultures | Plaque size (mm) | |
|---|---|---|---|---|---|
| | | | | 30° C. | 35° C. |
| S 4/63 | Washington, D. C. ('63) | TC | ? | 0.60 ± 0.10 | 1.52 ± 0.22 |
| K 9/67 | Kentucky ('67) | Kidney | 3 | ND[c] | 1.46 ± 0.07 |
| N.J. 2/68 | New Jersey ('68) | Kidney | 2 | ND | 1.52 ± 0.10 |
| N.Y. 6/69 | New York ('69) | Vagina | 4 | 0.48 ± 0.12 | 1.50 ± 0.06 |
| SL/18 | Maryland ('65) | Spleen | 2 | ND | 1.49 ± 0.10 |
| M 9/68 | Maine ('68) | Kidney | 2 | ND | 1.54 ± 0.08 |
| F 8/73 | New Yori ('73) | Lung | 2 | 0.56 ± 0.07 | 1.45 ± 0.12 |
| B 10/73 | Massachusetts ('73) | Kidney | 3 | 0.62 ± 0.03 | 1.46 ± 0.10 |
| N.J. 2/74 | New Jersey ('74) | Kidney | 3 | ND | 1.52 ± 0.10 |
| PR/1 | Missouri ('67) | TC | 4 | ND | 1.49 ± 0.22 |

[a]Samples were neonatal pup tissues received for diagnosis or infected DKC cultures. The exceptions were strains 0 3/66 and N.Y. 6/69, which were isolated from mature female dogs. TC indicates canine kidney cell cultures.
[b]See text for natural history of mP variant of strain F-205.
[c]ND, Not done.

When the wild (MP) strains of canine herpesvirus are tissue culture passaged at optimal temperatures neither a reduction in virulence for newborn pups nor the emergence of plaque variants is observed.

However, when the MP strains are tissue culture passaged in a canine herpesvirus growth supporting medium at suboptimal growth sustaining temperatures, i.e. <33° C., preferably between about 28° C. and about 33° C., there appears in a very few passages, i.e. usually less than ten and frequently 2 or 3, a substantial number of small plaques which contain a canine herpevirus small plaque (mP) variant which lacks pathogenicity for newborn pups, but which serves as a vaccine to impart resistance to dogs against virulent MP canine herpesvirus strains.

The small plaque (mP) variant can be cloned and is temperature and tissue culture passage stable. The mP variant has a plaque size at 35° C. less than about 0.7 times the diameter of the MP strain from which it is derived. For example, in contrast to the wild type MP virus, (Table 1 supra) the mP variant (e.g. strain F-205) produced plaques at 35° C. that were approximately one-half the size of the wild-type (MP) virus plaques (FIG. 1). Similar consistency in plaque size and character was observed at the 30° C. growth temperature. At the lower temperature, however, plaques produced by the MP virus were approximately 60% the diameter observed at 35° C. Plaques formed by the mP virus at 30° C. were 86% the size produced at 35° C. Plaques formed under a methylcellulose medium did not differ significantly from those produced when agarose was used in the overlay medium.

The above observations are based upon the following examples with the F-205 strain of CHV, found fully virulent for newborn pups after 312 passages in DKC cultures incubated at 35° C. gave rise to plaques of the MP type. This type was characteristic of 12 additional CHV field strains that had been passaged fewer than four times in DKC cultures. However, after fewer than 20 additional passages at low temperature (30° C.), a stable mP variant of strain F-205 was the principal viral type. Since cloned mP virus retained the small plaque characteristic after more than 60 passages at 30° C., the mP marker appears to represent a stable biological property inherent to the genome of the variant virus.

EXAMPLE

Virus strains and cell cultures

The characteristics of CHV (strain F-205) and methods for its cultivation and assay have been previously described; Carmichael et al, *Am. J. Vet. Res.,* 26: 802–814 (1965); Carmichael et al, *Proc. Soc. Biol. Med.,* 120: 644–650 (1966). Additional isolates (See Table 1, supra) were recovered from tissue specimens submitted to the James A. Baker Institute for Animal Health, New York State College of Veterinary Medicine, Cornell University, Ithaca, New York, for viral culture or, in some instances, were obtained from other investigators.

Standard plaque medium for cloning was double-strength Eagle minimal essential medium (MEM; BBL), supplemented with 10% fetal bovine serum (FBS) and 0.5% lactalbumin hydrolysate (LAH) mixed with an equal volume of 2% agarose (Sea Plaque).

For plaque size determinations and viral assays, monolayer DKC cultures in 60-mm plastic plates were inoculated with 0.2 ml amounts of serial 10-fold dilutions of virus and absorbed for 1.5 h. at room temperature. After the absorption period, 5-ml amounts of MEM, supplemented with 5% FBS and 0.5% LAH that contained 1% methylcellulose (Hotchin, *Nature* (*London* ), 175: 352 ( 1955)) were added to each plate, and cultures then were incubated in a humidified 5% $CO_2$ atmosphere at 30° or 35° C. After 5 days of incubation, the viscous medium was decanted, and plates were fixed for 10 min. with 10% neutral formalin, rinsed in tap water, and then stained with 1% aqueous crystal violet solution. Plaque size was measured with a calibrated ocular micrometer. At least 100 plaques were measured for each strain studied.

Cultures of canine spleen cells were prepared by rapidly stirring, at room temperature, minced tissue in MEM without added trypsin. After 2 h., the suspensions were filtered through six layers of sterile gauze and diluted in growth medium (MEM supplemented with 10% FBS and LAH) to contain approximately $10^6$ cells/ml. Cultures were prepared in 25-$cm^2$ plastic flasks, using 5-ml amounts per flask. After 24 h., cultures were shaken, and the adherent cells, which were more than 90% mononuclear, were used for viral growth studies.

Natural History of mP Variant

In an attempt to select strains of reduced virulence, CHV (strain F-205) was rapidly transferred (2-day intervals), for a total of 312 passages, using terminal dilutions at approximately each 10th passage. Each 10th DKC passage was harvested and stored frozen at −70° C. in a stabilizing menstruum for later tests of pathogenicity in newborn pups and for the study of certain biological properties, as noted later. After 312 passages at 35° C., neither a reduction in virulence for newborn pups nor the emergence of plaque variants was observed.

The 312th DKC passage virus, which caused fatal infections and was uniform with regard to plaque chacterstics under a 1% methylcellulose overlay, was then rapidly transferred at 30° C. After approximately 20 passages at 30° C., subtle changes in the cytopathic effects (CPE) were observed in tube cultures, and the principal plaque type measured approximately one-half the diameter (0.75 mm) of the parental strain. After plaque purification, using an agarose overlay medium, a typical mP clone was selected for further passage and study. It was designated CHV-mP to distinguish it from the macroplaque (MP) parental virus. The mP variant has retained its unique plaque characteristics after 66 passages in DKC cultures incubated at 30° C.

Heat Inactivation

Freshly harvested 24-h. cultures of the mP and MP strains were rapidly frozen and thawed three times. Cell debris was removed by centrifugation at 600×g for 10 min. at 4° C., and clarified virus in MEM containing 10% FBS was placed in a water bath at 38° C. Aliquots were removed at intervals for infectivity titrations. Virus survival was plotted versus time.

Immunodiffusion

Antigens for immunodiffusion tests were prepared from mP and MP virus grown in 75-cm$^2$ plastic flasks. When cultures had evidence of extensive CPE, the adherent cells were scraped off the flask with a rubber policeman. After centrifugation at 600×g, the fluid portions were discarded and the cell portions were taken up in one-tenth the original volume in distilled water, frozen and thawed three times, and then clarified by low-speed centrifugation. The supernatant portions then were placed in cellophane dialysis tubing and dialyzed for 24 h. at pH 10.3 (glycine-NaOH buffer) to dissociate viral subunits. After overnight dialysis against 0.15 M phosphate-buffered saline, pH 7.2, the antigen preparation was stored frozen at −70° C. Tests were performed on 2.5- by 7.5- cm plastic immunodiffusion slides, using 0.6% agarose in phosphate-buffered saline. An eight-well pattern was used to compare all permutations of mP or MP antigens with the respective hyperimmune antisera that had been prepared in specific-pathogen-free beagles.

Tests for Virulence

A total of 21 specific-pathogen-free beagle pups (four litters) from the Institute's disease-free colony were used. All animals were obtained from bitches without detectable CHV-neutralizing antibody. Serum neutralization methods have been described previously; Carmichael, *J. Am. Vet. Med. Assoc.*, 156: 1714-1721 (1970. Thirteen neonatal pups (two litters) were given intraperitoneal or oral-nasal inoculations within the first 48 h. of birth, since pups rapidly develop resistance to generalized, usually fatal, infections after that time; Carmichael et al, *J. Infect. Dis.*, 120: 669-678 (1970).

To examine effects of immunosuppression on the pathogenicity of the mP variant, eight 2-week-old pups were divided into four groups, each consisting of two pups. In one group, each pup was inoculated with 0.5 ml of goat anti-dog thymoctye serum (ATS) at the time of infection with mP virus and again on post-inoculation days 2 and 4. Another group of two pups was given mP virus but no ATS. The thid group was inoculated with CHV-MP, and the fourth received CHV-MP plus ATS. Viral doses were $10^{5.2}$ 50% tissue culture infective doses (TCID$_{50}$) (CHV-mP) or $10^{4.8}$ TCID$_{50}$ (CHV-MP). The ATS, prepared in our laboratory, had a canine lymphocyte cytotoxicity titer of 1.320. After two injections (0.5 ml/kg), there was a marked (>80%) diminution in the normal responses of canine peripheral blood lymphocytes to phytohemagglutinin, severe thymic atrophy, and profound alteration in the course of CHV infection in normally resistant 2-week-old pups.

While primary dog kidney cell (DICC) cultures are the cultures of choice, the growth supporting medium employed as the tissue culture for virus passage is not unduly critical. Any tissue culture medium can be employed which supports canine herpesvirus growth. A number of such media are known in the art.

Based upon the above and similar experimental work the following observations are made:

Growth characteristics of the MP and mP strains in DKC cultures incubated at 30° and 35° C.

Growth of the mP strain in DKC cultures at 35° C. was not restricted (FIG. 2). When viral inputs were approximately equal, the titers of inputs were approximately equal, the titers of CHV-mP, after 24 h. of growth, were at least 0.8 log$_{10}$ greater than those of the MP strain. CPE of the two strains were similar, but not identical. Cells infected with the mP variant generally were more swollen and refractile than those infected with MP virus, and they tended to clump around the edges of a plaque. Cells infected with the MP strain were uniformly rounded, and they detached readily from the growth surface. Syncytia were not observed with either virus. A consistent feature of the mP variant was the late appearance of CPE in relation to the production of infectious virus.

Both strains grew more slowly at 30° C.; however, growth of the MP virus was somewhat more restricted at this temperature. An additional difference between the MP virus and the mP variant was the amount of infectious virus released (Table 2). The MP virus was significantly more cell associated throughout the growth period than was the mP variant.

TABLE 2.

| | Cell-associated virus released MP and mP canine herpesvirus grown at 35° C. | | | | | |
|---|---|---|---|---|---|---|
| | Virus Titer$^a$ | | | | Virus Release (%) | |
| Incubation | CHV-MP$^b$ | | CHV-mP | | | |
| time (h) | Cells | Fluid | Cells | Fluid | MP | mP |
| 12 | 4.8 | 1.8 | 3.2 | 1.5 | 0.1 | 1.9 |
| 18 | 5.5 | 2.5 | 4.8 | 3.0 | 0.1 | 1.6 |
| 24 | 5.5 | 2.8 | 5.2 | 3.5 | 0.2 | 1.9 |

$^a$Log$_{10}$ TCID$_{50}$/0.2ml.
$^b$Viral inputs were $10^{6.3}$ (MP) and $10^{5.8}$ (mP) per flask culture.

Inactivation at 38° C.

Results (FIG. 3) suggested that the MP strain is somewhat more heat labile than the MP virus; however, the differences were slight.

(I-661), there were no macroscopic lesions. Virus was not recovered from the other three pups that were infected with mP virus and then euthanized 6 or 8 days later. Pups that were allowed to survive did not have signs of illness, and they all developed CHV-neutralizing antibody by post-inoculation week 3.

TABLE 3.

Tests for virulence of MP and mP variant CHV in newborn pups

| Pup No. | Plaque Type | Viral dose (TCID$_{50}$) | Inoculation route[a] | Survival or death[b] | Macroscopic lesions[c] | Viral isolation ($\log_{10}$ TCID$_{50}$/0.2 g of tissue) | | | | |
|---|---|---|---|---|---|---|---|---|---|---|
| | | | | | | Nasopharynx (days) | Kidney | Spleen | Liver | Cerebellum | Lung |
| I-658 | MP | $10^{4.8}$ | i.p. | D(5) | Severe | +(2-5) | 4.5 | 3.5 | 4.5 | 2.5 | 3.5 |
| I-659 | MP | $10^{4.8}$ | O/N | D(6) | Severe | +(2-6) | 4.5 | 3.0 | 4.0 | 2.5 | 3.5 |
| I-660 | mP | $10^{5.2}$ | i.p. | E(6) | None | +(3-5) | 1.0 | 2.5 | <1 | <1 | 2.5 |
| I-661 | mP | $10^{5.2}$ | O/N | E(6) | None | +(2-6) | <1 | <1 | 1.0 | <1 | <1 |
| I-662 | mP | $10^{5.2}$ | i.p. | E(6) | None | +(3-5) | <1 | <1 | <1 | <1 | <1 |
| II-644 | MP | $10^{4.5}$ | i.p. | D(6) | Severe | +(2-6) | 5.0 | 3.5 | 3.5 | 2.5 | 4.5 |
| II-645 | MP | $10^{4.5}$ | O/N | D(8) | Severe | +(2-6) | 5.5 | 4.5 | 4.0 | 3.0 | 5.0 |
| II-646 | mP | $10^{5.0}$ | i.p. | E(6) | None | +(2-6) | <1 | <1 | <1 | <1 | <1 |
| II-647 | mP | $10^{5.0}$ | i.p. | S[d] | —[e] | +(2-4) | — | — | — | — | — |
| II-648 | mP | $10^{5.0}$ | i.p. | S | — | +(2-5) | — | — | — | — | — |
| II-649 | mP | $10^{5.0}$ | O/N | E(8) | None | +(2-4) | <1 | <1 | <1 | <1 | <1 |
| II-650 | mP | $10^{5.0}$ | O/N | S | — | +(2-5) | — | — | — | — | — |
| II-651 | mP | $10^{5.0}$ | O/N | S | — | +(2-4) | — | — | — | — | — |

Antigenic comparisons

Antisera raised in dogs against the MP field strain (F-205) neutralized the homologous virus and the mP variant to the same extent in plaque reduction and kinetic neutralization tests. Immunodiffusion analysis also failed to reveal antigenic differences, for two precipitin lines of identify were observed between the mP and MP viral antigens and the respective antisera.

Growth and mP and Mp strains in splenic macrophage cultures at 30° and 37° C.

Splenic macrophage cultures maintained at 30° C. continued to release small amounts of infectious virus (~10 plaque-forming units/0.2 ml) throughout the 70-h. incubation period; however, there was scant growth of either virus (FIG. 4). Growth of the mP virus was restricted to a greater extent than that of the MP strain in macrophage cultures incubated at 37° C. At 37° C. the mP virus persisted intracellularly without decrease in titer for 24 h., but infectious virus then declined. Extracellular virus was not detected. By 60 h. postinfection, the mP virus no longer could be detected; however, cell-associated MP virus still was present ($3 \times 10^3$ plaque-forming units/0.2 ml) after 70 h. of incubation. At this time, cell cultures were <90% viable as judged by trypan blue exclusion tests.

Virulence of the MP and mP strains for newborn pups

The response of pups to inoculations with MP and mP virus are summarized in Table 3. The MP strain produced generalized and fatal infections in all pups, regardless of the route of inoculation. High viral titers were found in all tissues examined. In contrast, the mP variant was markedly reduced in virulence, for none of the pups had signs of illness. Nevertheless, mP virus was recovered from the nasopharynx of all pups for 4 to 6 days after inoculation. Although small amounts of virus were recovered from kidney, spleen, and lung tissues of one pup (I-660) euthanized 6 days after intraperitoneal inoculation and from the liver of an additional pup Effects of ATS CHV growth was greatly restricted in the 2-week-old pups given the Mp or mP virus (groups 1 and 2; Table 4); however, the pups that received ATS at the time of inoculation with MP virus (group 4) dies by the 6th post-inoculation day. Pups that were inoculated with mP virus and then treated with ATS did not have signs of illness; however, at necropsy, their thymus glands were approximately one-third the weight of the thymuses from the non-treated animals. None of the pups that received mP virus had prominent macroscopic lesions, although occasional small areas of focal necrosis, but no hemorrhages, were observed microscopically in the lung and liver of one pup (no. 4). The lesions were similar to those seen in 2-week-old pups that were given MP virus but not ATS. In contrast, the pups (no. 7 and 8) given MP virus and ATS had high viral titers in several organs. Remarkably high titers were found in the brain.

Microscopic lesions in the inoculated 2-week-old pups that were given the MP virus but no ATS were disseminated small foci of interstitial pneumonitis, necrosis of occasional hepatocytes, and minute areas of renal hemorrhage and focal interstitial necrosis, with minimal inflammatory changes. Contrasting with these modest lesions were the prominent changes observed in the MP-inoculated pups treated with ATS (group 4). They consisted of interstitial pneumonitis, with alveolar necrosis and hemorrhages, necrotic foci throughout the liver, and multiple foci of necrosis and hemorrhages in the renal cortices, with both tubular and glomerular destruction. Central nervous system changes consisted of disseminated focal enephalitis, necrosis of neuronal and astroglial cells with mononuclear cell infiltrations, and segmental leptomeningitis. Other lesions typical of CHV infection of neonatal puppies also were observed in these animals; Carmichael, *J. Am. Vet. Med. Assoc.*, 156: 1714–1721 (1970); Carmichael et al., *Am. J. Vet. Res.*, 26: 802–814 (1965); Pryde, supra.

TABLE 4.

Response of 2-week-old pups to CHV (MP or mP) and effects of ATS

| Group | Plaque type inoculated (pup no.) | Illness | Macroscopic lesions at necropsy[a] | Thymus wt (g) | Nasolpharynx (days) | Viral isolation ($\log_{10}$ TCID$_{50}$/0.2g) | | | | |
|---|---|---|---|---|---|---|---|---|---|---|
| | | | | | | Kidney | Spleen | Liver | Lung | Cerebellum |
| 1 | CHV-mP (1) | None | None | 1.8 | +(2–7) | <1 | <1 | <1 | <1 | <1 |
| | (2) | None | None | 2.0 | +(2–5) | <1 | <1 | <1 | 1.2 | <1 |
| 2 | CHV-mP (3) + | None | None | 0.7 | +(2–8) | <1 | 1.0 | <1 | 1.0 | <1 |
| | ATS (4) | None | None | 0.5 | +(2–8) | <1 | 0.8 | 1.0 | 1.5 | <1 |
| 3 | CHV-MP (5) | None | Mild | 1.9 | +(2–8) | 1.0 | <1 | 1.0 | 2.5 | <1 |
| | (6) | None | Mild | 1.8 | +(2–8) | 0.8 | <1 | <1 | 2.0 | <1 |
| 4 | CHV-MP (7) + | Died[b] | Severe | 0.5 | +(2–4) | 3.5 | <1 | 2.5 | 4.5 | 3.5 |
| | ATS (8) | Died | Severe | 0.6 | +(2–6) | 4.0 | 3.5 | 2.0 | 5.5 | 2.5 |

[a] See text for lesion descriptions
[b] Pups no. 7 and 8 dies on postinfection days 4 and 6, respectively. Surviving pups were euthanized at day 8.

The above studies demonstrate that the mP virus had additional biological properties that distinguished it from the parental MP virus. Notwithstanding the subtle, but nevertheless distinct, differences between the MP and mP strains in the character of cytopathology, the times of onset of CPE, the rates and amounts of virus produced at 30° and 35° C., viral persistence in canine spleen monocyte cultures, and, of lesser significance, the rates of inactivation at 38° C., there were distinct differences in their virulence for pups.

The MP (wild-type) virus was highly virulent for newborn pups and for 2-week-old animals that had received ATS at the time of infection. The mP variant, however, was clearly an attenuated strain. Although the mP variant persisted for several (4 to 6) days in the nasopharynx, it rarely was recovered from other tissue sites favored by the MP virus, and then only in small amounts.

Association between small plaque size and reduced virulence has been reported for plaque variants or mutants of other herpesviruses [Darlington R. W. et al. "Replication-biological aspects", in *The herpesviruses* (Kaplan ed.) Academic Press Inc., New York (1973), pp 93–132; Rapp, F., et al., *Proc. Soc. Exp. Biol. Med.*, 116: 361–365 (1964)], the most noteworthy being MDHV [Biggs et al., "Biological properties of a number of Marek's disease virus isolates", in *Oncogenesis and herpesviruses* (Biggs et al., ed.) WHO International Agency for Research on Cancer, Lyon (1972) pp 88–94; Cho, *Avian Dis.*, 20: 324–331 (1976); Darlington et al. supra]. The mP-CHV, however, did not behave as an attenuated host range, temperature-sensitive mutant, as described for the large- and small- plaque mutants of HVH-2; Darlington et al, supra; Korment et al, supra. It did not regularly engender the formation of syncytia, as described for the CHV-BR strain, Poste, supra, or occur as a naturally attenuated plaque variant, as described for field isolates of MDHV, but it originated after less than 20 passages in DKC cultures incubated at 30° C. after prolonged culture (312 passages) at 35° C. Unfortunately, the precise passage at which the mP variant emerged could not be determined, but it was the dominant type after 20 passages at 30° C.

Unlike the antigenic change (loss of the "A antigen") that has been associated with the attenuation of MDHV after prolonged passage in chicken renal cell cultures, Purchase et al., *Infect. Immun.*, 3: 295–303 (1971), antigenic markers specific for the attenuated CHV-mP strain were not detected.

Immunological tests

The following three examples demonstrate the efficacy of the mP canine herpesvirus strain in imparting resistance to wild-type virulent canine herpesvirus. Because signs of illness are absent in dogs older than one week of age, (Carmichael et al, *J. Am. Vet. Med. Assoc.* 156: 1714–1721 (1970) vaccine trials were designed so as to demonstrate efficacy based upon relative duration of viral shed (equivalent to viral growth in host) following challenge inoculation with virulent (mP) virus.

Littermate SPF Beagle dogs each were inoculated intramuscularly (1 M) or oral/nasally (O/N) with $10^{5.2-5.8}$ tissue culture infective doses (TCD$_{50}$) of mP CHV. Blood samples were taken prior to vaccination and before challenge-inoculation with virulent (MP, macroplaque) CHV (strain F-205), and thereafter at intervals. Nasal-pharyngeal swab samples were collected for a period of 2 weeks after both vaccination and challenge-inoculation for viral isolations. Results (serologic responses, signs of illness, virus shedding) were recorded for vaccinated and unvaccinated (control) animals that received challenge inoculations at the same time as the vaccinates.

EXAMPLE

The first of three groups of pups was vaccinated at four months of age and challenge-inoculated three months later (D800 through 802). Control animals were D803–804. See Table 5. Vaccine virus given IM did not spread to unit-contact controls over a period of three months. Neither vaccinated animals nor controls had signs of illness post-vaccination or post-challenge. This was considered to be a normal response since immunity to this virus must be based on the relative restriction of viral shedding of vaccinates and controls.

TABLE 5.

Intramuscular vaccination at 4 months of age (CHV mP)

| Dog | Post-vac. virus shed (days) | Pre-chall. SN antibody (3 mo. p.v.) | Post-chall. virus shed (days) | Conclusion |
|---|---|---|---|---|
| Vaccinates | | | | |
| D800 | 0 | 1:16 | 2(MP) | Immune |
| D801 | 0 | 1:4 | 0 | Immune |
| D802 | 0 | 1:4 | 0 | immune |
| Controls | | | | |
| D803 | — | <1:2 | 8(MP) | Not immune |
| D804 | — | <1:2 | 11(MP) | Not immune |

EXAMPLE

The second group was vaccinated oral/nasally at three days of age and challenge-inoculated one month later, with appropriate controls (D612-617 vaccinated; D618-619 controls). See Table 6.

The mP (attenuated) virus was shed from 1-7 days after O/N inoculation, in contrast to the MP virus that is commonly shed in copious amounts for approximately 14 days (8-17 days in more than 30 dogs studied). Low antibody titers were generated that did not completely exclude the MP challenge virus. However, there was evidence of an anamnestic response (results of 8-day serology) in vaccinated dogs, with accelerated rejection of the challenge MP virus, as compared with controls. An immune response with reduction in viral shed is clearly evident. No signs of illness were observed in vaccinated or control dogs. Although not an object of this trial, it may be concluded further (confirming published reports from this laboratory, Infection and Immunity 20:108-114, April 1978) that mP is avirulent for neonatal pups.

TABLE 6.

Oral-nasal vaccination at 3 days of age (SPF beagles)

| Dog | Post-vacc. virus shed | Pre-chall. antibody(SN) | Post-chall. virus shed(days) | Antibody 8 day post-chall. | Conclusion |
|---|---|---|---|---|---|
| Vaccinates | | | | | |
| D612 | 1-5(days)mP* | 1:8 | 1-7 (MP) | 1:32 | Immune |
| D614 | 1-7 mP | 1:4 | 2-7 (MP) | 1:16 | Immune |
| D615 | 1-7 mP | 1:4 | 2-8 (MP) | 1:12 | Immune |
| D616 | 1-4 mP | 1:8 | 2-3 (MP) | 1:16 | Immune |
| D617 | 1-4 mP | 1:8 | 2-5 (MP) | 1:16 | Immune |
| Controls | | | | | |
| (non-contact) | | | | | |
| D618 | — | <1:2 | 1-12 | 1:4 | Not immune |
| D619 | — | <1:2 | 1-16 | 1:8 | Not immune |

*mP = attenuated virus
MP = virulent virus

EXAMPLE

The third group (D54-57) was vaccinated intramuscularly at 2 months of age. Animals were challenge-inoculated one month later. 2-months later all dogs received corticosteroid (dexamethasone, 1 mg/day for 5 days), a drug shown to cause recrudescence of persistent CHV. Swab samples were collected during and following steroid treatment for a total period of 12 days. Virus recovered following steroid treatment was analyzed for plaque type (MP=virulent, mP=vaccine strain). See Table 7.

Viral shed did not occur following initial vaccination (IM route), and there was no spread of virus to in-unit contacts. Following challenge viral shed was again reduced. Relative amounts of virus recovered (generally less than 10 $TCD_{50}$) was significantly less in vaccinates than controls (100 to 10,000 $TCD_{50}$). All vaccinates developed low SN antibody titers. Within 8 days following challenge, titers did not change, indicating minimal immune response to challenge virus, i.e. limited viral growth. Following corticosteroid drug treatment (dexamethasone), there was no recrudescence of the vaccine virus. MP virus (virulent) was recovered, however, from the control dogs that had received challenge inoculums 2 months previous to drug treatment, and which had been negative to viral isolation attempts (3×weekly) during the period following initial viral shedding and steroid treatment.

TABLE 7.

Host-response to MP and persistence of virus as revealed by viral recrudescence following steroid treatment

| Dog | Post-vacc. virus shed (days) | Pre-chall. SN antibody titer | Post-chall. virus shed (days) | Immune | Viral re-excretion following steroid treatment (2 mo. post-chall.) |
|---|---|---|---|---|---|
| Vaccinates | | | | | |
| 54 | 0 | 1:16 | 1-5 | Yes | Neg. |
| 55 | 0 | 1:8 | 1-4 | Yes | Neg. |
| 56 | 0 | 1:8 | 2-7 | Yes | Neg. |
| 57 | 0 | 1:6 | 2-4 | Yes | Neg. |
| Controls | | | | | |
| 58 | — | <1:2 | 1-16 | No | Pos. (3-9 day; MP virus) |
| 59 | — | <1:2 | 1-14 | No | Pos. (5-10 day; MP virus) |

The microplaque (mP) variant of CHV (strain F-205) is available from the James A. Baker Institute for Animal Health, New York State College of Veterinary Medicine, Cornell University, Ithaca, New York 14853, upon request.

I claim:

1. A method of increasing the resistance of dogs to Canine Herpesvirus infection which comprises inoculating susceptible pups or bitches prior to exposure to Canine Herpesvirus with a vaccine comprising a microplaque mP variant which has a plaque size about 0.7 times the diameter of the original Canine Herpesvirus isolate, said mP variant engendering resistance to virulent Canine Herpesvirus induced disease in the pups or the pups of said bitches.

2. The method of claim 1 wherein said small plaque-forming Canine Herpesvirus vaccine comprises a virus prepared by a process comprising the steps of:
   (a) inoculating a Canine Herpesvirus supporting medium with an isolate of Canine Herpesvirus
   (b) serially passing the virus at a suboptimal growth temperature less than about 33° C. until a substantial number of small plaques are formed which contain a Canine Herpesvirus which has a plaque size when grown at 35° C. less than about 0.7 times the diameter of the original Canine Herpesvirus isolate.

3. The method of claim 2 wherein a small plaque forming Canine Herpesvirus virus produced in step (b) is cloned and serially passaged in Canine Herpesvirus growth supporting medium to increase the virus titer.

4. The method of claims 2 or 3 where the suboptimal growth temperature is between about 28° C. and about 33° C.

5. A method of forming a small plaque variant reduced pathogenicity Canine Herpesvirus which comprises:
 (a) inoculating a Canine Herpesvirus supporting medium with an isolate of Canine Herpesvirus, and
 (b) serially passing the virus at a suboptimal growth temperature less than about 33° C. until a substantial number of small plaques are formed which contain a Canine Herpesvirus which has a plaque size when grown at 35° C. less than about 0.7 times the diameter of the original Canine Herpesvirus isolate.

6. The method of claim 5 wherein a small plaque forming Canine Herpesvirus virus produced in step (b) is cloned and serially passaged in Canine Herpesvirus growth supporting medium to increase the virus titer.

7. The method of claims 5 or 6 where the suboptimal growth temperature is between about 28° C. and about 33° C.

8. A method of increasing the resistance of dogs to Canine Herpesvirus infection which comprises inoculating susceptible pups or bitches prior to exposure to Canine Herpesvirus with a vaccine comprising a microplaque mP variant of Canine Herpesvirus strain F-205 which has a plaque size of 0.7 times the diameter of the original Canine Herpesvirus strain F-205 isolate, said mP variant engendering resistance to virulent Canine Herpesvirus induced disease in the pups or the pups of said bitches.

9. The method of claim 8 wherein said small plaque-forming Canine Herpesvirus vaccine comprises a virus prepared by a process comprising the steps of:
 (a) inoculating a Canine Herpesvirus supporting medium with Canine Herpesvirus strain F-205; and
 (b) serially passing the virus at a suboptimal growth temperature less than about 33° C. until a substantial number of small plaques are formed which contain a Canine Herpesvirus which has a plaque size when grown at 35° C. less than about 0.7 times the diameter of the original Canine Herpesvirus isolate.

10. The method of claim 9 wherein a small plaque forming Canine Herpesvirus virus produced in step (b) is cloned and serially passaged in Canine Herpesvirus growth supporting medium to increase the virus filter.

11. The method of claims 9 or 10 where the suboptimal growth temperature is between 28° C. and about 33° C.

12. A method of forming a small plaque variant reduced pathogenicity Canine Herpesvirus which comprises:
 (a) inoculating a Canine Herpesvirus supporting medium with Canine Herpesvirus strain F-205; and
 (b) serially passing the virus at a suboptimal growth temperature less than about 33° C. until a substantial number of small plaques are formed which contain a Canine Herpesvirus which has a plaque size when grown at 35° C. less than about 0.7 times the diameter of the original Canine Herpesvirus isolate.

13. The method of claim 12 wherein a small plaque forming Canine Herpesvirus produced in step (b) is cloned and serially passaged in Canine Herpesvirus growth supporting medium to increase the virus titer.

14. The method of claims 12 or 13 where the suboptimal growth temperature is between about 28° C. and about 33° C.

* * * * *